(12) United States Patent
Caballes

(10) Patent No.: US 9,707,093 B2
(45) Date of Patent: Jul. 18, 2017

(54) ELASTOMERIC ARTIFICIAL JOINTS AND INTERVERTEBRAL PROSTHESIS SYSTEMS

(71) Applicant: Ervin Caballes, Denver, CO (US)

(72) Inventor: Ervin Caballes, Denver, CO (US)

(*) Notice: Subject to any disclaimer, the term of this patent is extended or adjusted under 35 U.S.C. 154(b) by 0 days.

(21) Appl. No.: 14/815,411

(22) Filed: Jul. 31, 2015

(65) Prior Publication Data

US 2015/0335444 A1    Nov. 26, 2015

Related U.S. Application Data

(63) Continuation of application No. 13/680,562, filed on Nov. 19, 2012, now Pat. No. 9,125,753.

(60) Provisional application No. 61/600,516, filed on Feb. 17, 2012.

(51) Int. Cl.
| | |
|---|---|
| *A61F 2/44* | (2006.01) |
| *A61F 2/30* | (2006.01) |
| *A61F 2/40* | (2006.01) |
| *A61F 2/32* | (2006.01) |
| *A61F 2/38* | (2006.01) |

(52) U.S. Cl.
CPC ............ *A61F 2/442* (2013.01); *A61F 2/30* (2013.01); *A61F 2/32* (2013.01); *A61F 2/38* (2013.01); *A61F 2/40* (2013.01); *A61F 2/4425* (2013.01); *A61F 2/3836* (2013.01); *A61F 2002/3007* (2013.01); *A61F 2002/3038* (2013.01); *A61F 2002/3065* (2013.01); *A61F 2002/30133* (2013.01); *A61F 2002/30387* (2013.01); *A61F 2002/30563* (2013.01); *A61F 2002/30662* (2013.01); *A61F 2002/30911* (2013.01); *A61F 2002/443* (2013.01)

(58) Field of Classification Search
CPC ...... A61F 2/44; A61F 2/30; A61F 2/32; A61F 2/442; A61F 2/4425
USPC ............................................ 623/17.11–17.16
See application file for complete search history.

(56) References Cited

U.S. PATENT DOCUMENTS

| | | |
|---|---|---|
| 3,938,198 A | 2/1976 | Kahn et al. |
| 4,231,122 A | 11/1980 | Koeneman et al. |
| 4,759,766 A | 7/1988 | Buettner-Janz et al. |
| 4,911,718 A | 3/1990 | Lee et al. |

(Continued)

FOREIGN PATENT DOCUMENTS

EP         2 377 495 A1    10/2011

*Primary Examiner* — Christopher Beccia
(74) *Attorney, Agent, or Firm* — Lathrop & Gage LLP

(57) ABSTRACT

An elastomeric artificial joint and prosthesis system combining motion preservation and shock absorption through the interaction of core and endplate components. The core is comprised of: a "hub" having congruent concavity with the endplate surface allowing for rotation, translation, flexion and extension, orbital, lateral bending, and compression motion similar to that of a joint or natural intervertebral disc; a "flange" attached to the hub and able to move congruently with the hub, and having negative spaces providing an internal structure for an elastomer; and a bio-compatible elastomer casted around and through the flange providing shock absorption. The endplate has a low-friction surface and engages the elastomer, and a structural component that engages the vertebral endplate or bone surface. The device has medical applications such as in total joint arthroplasty, disc replacement, and industrial applications such as in robotics that are modeled to move similar to human anatomical motion.

19 Claims, 13 Drawing Sheets

(56) References Cited

U.S. PATENT DOCUMENTS

| | | | |
|---|---|---|---|
| 5,139,526 | A | 8/1992 | Skardoutos et al. |
| 6,280,404 | B1 | 8/2001 | Morinaka et al. |
| 6,585,770 | B1 | 7/2003 | White et al. |
| 6,936,071 | B1 | 8/2005 | Marnay et al. |
| 7,156,876 | B2 | 1/2007 | Moumene et al. |
| 7,689,320 | B2 | 3/2010 | Prisco et al. |
| 7,731,753 | B2 | 6/2010 | Reo et al. |
| 7,975,568 | B2 | 7/2011 | Zhang et al. |
| 8,038,718 | B2 | 10/2011 | Palm et al. |
| 8,361,150 | B2 * | 1/2013 | Zhang ............... B32B 15/08 623/17.11 |
| 2004/0247641 | A1 | 12/2004 | Felt et al. |
| 2005/0119752 | A1 | 6/2005 | Williams et al. |
| 2005/0197702 | A1 * | 9/2005 | Coppes ............... A61F 2/441 623/17.12 |
| 2007/0100454 | A1 * | 5/2007 | Burgess ............ A61B 17/025 623/17.14 |
| 2008/0046082 | A1 | 2/2008 | Lee |
| 2009/0222094 | A1 | 9/2009 | Belliard et al. |
| 2009/0222098 | A1 | 9/2009 | Trieu et al. |
| 2010/0076558 | A1 | 3/2010 | de Villers et al. |
| 2010/0168860 | A1 | 7/2010 | Reichen et al. |
| 2010/0324689 | A1 | 12/2010 | Obrigkeit et al. |
| 2011/0004313 | A1 | 1/2011 | de Villers et al. |
| 2011/0071635 | A1 * | 3/2011 | Zhang ............... B32B 15/08 623/17.11 |
| 2011/0137421 | A1 * | 6/2011 | Hansell ............. A61F 2/4425 623/17.16 |

\* cited by examiner

ELASTOMERIC ARTIFICIAL JOINTS AND INTERVERTEBRAL PROSTHESIS SYSTEMS

CROSS-REFERENCE TO RELATED APPLICATIONS

This application claims priority from U.S. application Ser. No. 13/680,562, filed Nov. 19, 2012, and U.S. Provisional Patent Application No. 61/600,516, filed Feb. 17, 2012, both of which are incorporated by reference herein to the extent that there is no inconsistency with the present disclosure.

BACKGROUND OF THE INVENTION

This invention is in the field of artificial joints and intervertebral prosthetics which are able to retain at least some degree of natural motion while providing shock absorption and improved durability.

Degenerative changes in the joints of the human body and the intervertebral discs of the human spine can begin in early adulthood. Aging, wear and tear, and disease, such as osteoarthritis, can cause severe damage and loss to cartilage within the joints, often times requiring joint replacement or joint arthroplasty surgery. This includes all joints within human anatomy such as spinal endplate joints, spinal facet joints, hip, knee, shoulder, elbow, and cranial joints. Similarly, disc degeneration, annular tearing, nucleus herniations, and internal disc disruptions can cause disc material to extrude out of the annulus altering the elastic properties of the intervertebral disc, and are treated with disc replacement or disc arthroplasty surgery. Disc degeneration is of particular concern because the blood supply to the intervertebral discs diminishes at adulthood, therefore there is no regeneration of cells.

In joint replacement surgery, one or more surfaces of an arthritic or damaged joint is removed and replaced with an artificial joint, typically called a prosthesis. Joint replacement, or joint arthroplasty, is becoming more common with over approximately 750,000 Americans having a hip or knee replaced each year. While hip and knee replacement surgeries may be the most common, joint replacement can also be performed on other joints such as the shoulders, fingers, and ankles.

The current standard for treating degenerative disc disease and other spinal disorders is a decompression and fusion. Intervertebral disc, bone, and other material are removed to increase the spaces in which the spinal cord and nerves travel through the vertebral column. Mechanical fixation such as pedicle screws and rods are then implanted for initial structural support. Bone growth is then induced by the addition of materials such as bone graft and bone morphogenic proteins. In many cases, the intervertebral disc is completely removed and an allograft or a synthetic cage is implanted in the intervertebral disc space to restore proper disc height and assist in the fusion process. Spinal fusions, however, are not always favorable treatments because fusions disrupt the natural bio-mechanics of the spine by eliminating motion at the fusion site. Spinal fusions also increase the strain on the remaining motion segments of the spine.

Artificial joints are also used in prosthetic limbs, such as U.S. Pat. No. 6,280,404 ("Morinaka") and U.S. Pat. No. 5,139,526 ("Skardoutos"), where it is desirable for the joints to provide durability, shock absorption, and a range of motion similar to the natural body. Similarly, artificial joints are used in robotics where it is desirable to provide durability as well as movement similar to a human body, such as in surgical settings (U.S. Pat. No. 7,689,320 ("Prisco")) and assembly lines (U.S. Pat. No. 7,975,568 ("Zhang")).

There is a need for artificial joints, which include intervertebral prosthetics, that provide motion similar to the natural human body and have less of an effect on the bio-mechanics of the natural joint or spine if implanted into the body. Such joints must allow for rotation and torsion, translation, flexion, and extension, and lateral bending motion similar to that of a natural joint or intervertebral disc. Such implants must also ensure proper artificial joint height, prosthetic length, or disc height, and provide shock absorption similar to the compressibility of a natural joint or intervertebral disc.

Many previous artificial joint devices provide motion without shock absorption. To provide shock absorption, portions of the prosthetic, particularly the load bearing regions, can be coated with a compressible elastomer (see U.S. Pat. No. 3,938,198 ("Kahn")). However, most elastomeric devices do not isolate motion of the device from the shock absorption of the device. Using the elastomer for shock absorption in addition to motion of the device requires a softer elastomer, which is more susceptible to breakdown than harder elastomers. Harder elastomers generally are less susceptible to breakdown and have a lower coefficient of friction but provide less shock absorption.

Elastomeric devices are particularly susceptible to breakdown at the interface between the elastomer and the endplate. Previous devices typically do not use low friction materials at the interface between the elastomer and the end plate prosthetic and instead cement or bond the surfaces at this interface. However, bonding does not disperse the force related to the translational motion between the surfaces. In addition, solvents used in bonding material can degrade the elastomeric bonds and weaken the elastomeric properties.

U.S. Pat. No. 4,231,122 ("Koeneman") describes an artificial knee where the motion of the device does not occur at the interface of the elastomer and endplate. This device is then able to rely upon compression resilient elements made from elastomers to accommodate and carry the user's body weight. However, Koeneman notes that a pivot or pivotable assembly that incorporates a tubular body of elastomer in such a manner is only capable of extensive pivotal movement about a single axis. To provide some degree of rotation, this device requires two separate, parallel pivoting members to be implanted into the bone side by side. Each pivot member transfers the weight placed on the joint to a single pin as opposed to dispersing the weight across a wide surface. In addition, the elastomers are used as part of the motion limiter and as a foot, where both of these uses are not integrated with the motion of the device itself. Furthermore, the elastomers are disposed in between parts rather than casted into the device using negative spaces within the device.

U.S. Patent App. 2011/0004313 ("de Villers") describes a motion core in a prosthetic disc that is configured to slide relative to upper and lower surfaces; however, inserting a resilient material within the core as described in "de Villers" limits the amount of shock absorbing material and is less effective than if extended further from the center of articulation. This device also does not provide stress relief at the interface between the resilient material and the upper and lower parts of the core where fracture of the material or the bond between them is likely to occur.

U.S. Pat. No. 7,156,876 ("Moumene") describes a motion disc having an articulating core and a peripheral shock absorbing component; however, the "tenacious attachment" of the shock absorbing component to the endplate components has an ineffective interface where it is likely for the shock absorbing material to fracture or for the bonding between the surfaces to fail than if the surfaces were allowed to slide. In the embodiment without tenacious attachment, the articulation and shock absorption components are separate components in their motion, which increases stress on the shock absorbing material compared to combining these components in motion.

U.S. Pat. No. 6,936,071 ("Marnay") describes an intervertebral implant that also has two structural components that engage the natural vertebral endplates, and a core component with concavity for articulation. This device is an example of a group of devices that provide articulation without any shock absorbing component.

U.S. Patent App. 2010/0324689 A1 ("Obrigkeit") describes an artificial spinal implant comprising a thermoplastic elastomer that has a hard phase and soft phase. This invention uses a two phase elastomer to increase the durability of the elastomer; however, the device relies solely on the elastomer for movement. This device has a disadvantage because the entire load and movement of the device is transferred to the elastomer; thus, the elastomer is more susceptible to breakdown. This device also does not address the stress between the interface of the elastomer and the non-motion parts of the device.

U.S. Pat. No. 4,911,718 ("Lee") describes an intervertebral disc spacer that is comprised of an elastomer core that is reinforced by a fibrous laminate that is intended to simulate the natural nucleus pulposus and annulus fibrosus. Similar to "Obrigkeit," the entire load and movement of the device is placed on the elastomer and the device does not address the stress between the interface of the elastomer and the non-motion parts of the device. Also, "Lee," uses layers of elastomer with different hardness but has a soft core rather than a rigid core.

U.S. Pat. No. 4,759,766 ("Buettner-Janz") describes an intervertebral disc endoprosthesis comprising two concave end plates with an intermediate convex spacing piece. All three components have a plane guide rim. Similarly to "Marnay," this device does not contain any compressive material for shock absorption.

Foreign Patent No. EP 2 377 495 A1 ("Mingyan") describes a spinal implant that has two components, each with a surface that engages a vertebra and an interior surface that interfaces a core. Similarly to "Obrigkeit" and "Lee," the motion and load is placed into the viscoelastic material. Similar to "Moumene," there is an ineffective interface between the shock absorbing material and the endplate prosthetic. In addition, the viscoelastic material has no reinforcement such as a flange or a fibrous laminate as in "Lee."

U.S. Pat. No. 7,731,753 B2 ("Reo") describes upper and lower end plates separated by a compressible core member. The plates are wound together with high tensile strength fibers or other engagement mechanisms. In this device, the compressible core member is made of an elastomeric material, woven fabric, spring member or a combination of these materials. Similarly to "Obrigkeit," "Lee," and "Mingyan," this device relies on the core material to preserve motion between the vertebral bodies. This device relieves the stress between the interface of the core and the end plate prosthetics by using a cylindrical shaped core that can flatten out rather than allowing the interface between the core and the endplate to slide with low-friction as in the present device.

U.S. Pat. No. 6,585,770 B1 ("White") describes a device for supporting bony structures such as two vertebral bodies. This device is commonly used during procedures where a diseased vertebral body is partially or entirely removed and a cage is used to support the space between the vertebral bodies above and below the excised body. In contrast, in certain embodiments described herein, the present invention uses mesh cages for anchoring a prosthetic to bone or cartilage rather than supporting two bony structures.

Despite these advances in the field, there is still a need for more durable artificial joints and prosthetic implants that maintain motion and shock absorption and have less of an effect on the natural bio-mechanics of the human spine and joints. Previous inventions that use an elastomer for shock absorption do not contain a rigid internal structure for the elastomer, do not properly address the interaction between the elastomer and non-motion parts, and do not disperse the translational force at the interface between the elastomer and the endplate prosthetic using low-friction sliding.

SUMMARY OF THE INVENTION

The present invention provides a new application of elastomers as shock absorbing material in artificial joints, particularly prosthetics implanted into joints and the intervertebral disc spaces of the spine. While one embodiment of the present invention is particularly well suited for use as an intervertebral disc prosthesis, the present invention can also be adapted for use as implants in other joints, including but not limited to knee, hip, shoulder, finger and ankle joints, where retention of natural motion is desirable, and for use in artificial joints that are not implanted in the body where it is still desirable to provide motion similar to the human body, including but not limited to joints in artificial limbs and robotics.

In one embodiment, the present invention provides a motion-preserving artificial joint or prosthesis system comprising a core having a hub, a flange, and a biocompatible elastomer layer surrounding the flange. The hub contains a curved surface and is disposed within the flange so that at least a portion of the curved surface of the hub extends beyond the surface of the flange. The hub further comprises a rigid material able to maintain a selected prosthesis height. The flange is a rigid component able to provide internal structural support for the elastomer layer and may optionally contain one or more holes or negative spaces. In one embodiment of the device, only the flange is encased in elastomer. In another embodiment, the flange and at least a portion of the hub is encased with elastomer. In a further embodiment, the flange and the entire hub is encased with elastomer.

The artificial joint or prosthesis system also comprises an endplate comprising a structural component or anchor able to engage a natural vertebral endplate or a bone or cartilage surface at or near a joint. The endplate further comprises, opposite the structural engaging component, a first low-friction surface which engages the elastomer layer, and a second low-friction surface which engages the curved surface of the hub. In a further embodiment, the endplate further comprises a low-friction pad wherein the first low-friction surface which engages the elastomer layer is located on the surface of the low-friction pad. In another embodiment, the second low-friction surface which engages the curved surface of the hub is a concave surface. The artificial joint or prosthesis system as a whole and the individual components can be contoured or shaped to fit with an intervertebral space or within ball-and-socket, hinged, and fixed joint anatomies. For example, components including but not limited to the flange, endplate, and first and second low-friction surfaces may be generally planar or may be angled, curved or shaped (such as in a cup or concave shape).

The structural component or anchor, can be any means known in the art for attaching an artificial surface to a bone and/or cartilage surface, including but not limited to screws, keels, posts, teeth, spikes, clamps and combinations thereof. The structural component can optionally further comprise chemical means, such as biocompatible bonding agents, for attaching the endplate to the vertebral endplate or a bone or cartilage surface. In one embodiment, the present device has an improved anchor which comprises a cylindrical mesh cage to anchor the prosthesis to bony structures. The cylindrical shape of the anchor is an improvement from previous devices because it fits into the concavity of a natural vertebral endplate and provides a scaffold for bone growth through the negative spaces in the mesh. Previous inventions use a mesh cage for supporting bony structures, but not as an anchor for securing prosthetics to bone or cartilage. In a further embodiment, the present invention may or may not have a cap to cover the protrusions of the mesh because the surface area of the endplate prosthesis prevents the cage from subsiding into the bone further than desired.

The side of the core opposite from the endplate can comprise a structural component able to engage a bone and/or cartilage surface as described above; thereby allowing the core to be attached to one bone or cartilage surface while the endplate is attached to the opposing surface of the joint or intervertebral space. Alternatively, the core is attached to a second endplate which is attached to the bone/cartilage surface opposite from the first endplate. In one such embodiment, the hub contains a first and a second curved surface and is disposed within the flange so that at least a portion of the first curved surface of the hub extends above the surface of the flange and at least a portion of the second curved surface extends below the surface of the flange. A second endplate engages the core on the opposite side of the core from the first endplate, where the second endplate similarly comprises a first low-friction surface which engages the elastomer layer, and a second low-friction surface which engages the second curved surface of the hub. In a further embodiment, the second endplate further comprises a low-friction pad wherein the first low-friction surface of the second endplate which engages the elastomer layer is located on the surface of the low-friction pad. In a further embodiment, the second low-friction surface which engages the second curved surface of the hub is a concave surface. The second endplate also comprises a structural component able to engage a bone and/or cartilage surface. Attaching the one or more endplates to a natural vertebral endplate, or to a bone or cartilage surface, positions the artificial joint or prosthesis system into the intervertebral space or into the joint.

Thus, the present invention provides artificial joint and prosthesis devices where curved surface of the hub engages the second low-friction surface of the endplate providing a surface for motion, and has a flange for distributing the force placed on the prosthesis device. The compressible elastomer engages the first low-friction surface of the endplate and provides shock absorption when the endplate presses against the core.

In an embodiment, the artificial joint or prosthesis system is a motion-preserving intervertebral disc prosthesis system comprising a core having a hub, a flange, and a biocompatible elastomer layer surrounding the flange. The hub contains a curved surface and is disposed within the flange so that at least a curved surface of the hub extends above the surface of the flange. The hub further comprises a rigid material able to maintain a selected intervertebral disc height. The flange is a rigid component able to provide internal structural support for the elastomer layer and may optionally contain one or more holes or negative spaces. Metal surfaces involved in articulation of the device preferably are polished surfaces for reduced friction so that the curved surface of the hub preferably has a static coefficient of friction of 1 or less such as dry polished steel with itself. The curved surface of the hub may optionally be encased with an elastomer that has a static coefficient of friction of 1 or less. The disc prosthesis system also comprises an endplate having a structural component able to engage a natural vertebral endplate, a first low-friction surface which engages the elastomer layer, and a second low-friction surface which engages the curved surface of the hub. Optionally, the disc prosthesis system comprises a second endplate having a structural component able to engage a second natural vertebral endplate, a first low-friction surface which engages the elastomer layer, and a second low-friction surface which engages the curved surface of the hub which extends below the surface of the flange. In a further embodiment, one or both of the endplates further comprise a low-friction pad wherein the first low-friction surfaces which engages the elastomer layer are located on the surface of the low-friction pads.

The elastomer used herein is preferably molded around the flange and optionally a portion or all of the hub, preferably has a Shore hardness of approximately 60 A to 100 A, more preferably approximately 72 A to 95 A, even more preferably approximately 78 A. The elastomer also preferably has a modulus of elasticity of approximately 0.01 GPa to 0.1 GPa, more preferably approximately 0.01 GPa to 0.04 GPa, even more preferably approximately 0.03 to 0.04 GPa, Examples of such elastomers include, but are not limited to, the Biomer® Elast-Eon™ (AorTech International plc, Weybridge, Surrey, UK). The elastomer also preferably has a kinetic friction coefficient with dry steel of 1 or less, preferably approximately 0.1 to 1, or approximately 0.3 to 0.7.

Preferably the hub has a coefficient of friction of approximately 1.0 or less with dry polished steel, preferably approximately of 0.2 to 0.8, more approximately 0.3 to 0.6.

Preferably, the first low-friction surface that engages the elastomer layer has a coefficient of friction of approximately 0.3 or less with dry polished steel, preferably approximately of 0.1 to 0.3. Even more preferably, the first low-friction surface has a static coefficient of friction between 0.15 and 0.19 and a dynamic coefficient of friction between approximately 0.12 and 0.16 such as commercially available ultra-high molecular weight polyethylene (UHMWPE). Preferably, the second low-friction surface that engages the first or second curved surface of the hub has a coefficient of friction of approximately 0.5 to 1.5 with dry polished steel, more approximately 0.7 to 1.2, more approximately 0.8 to 1.1.

In embodiments where the flange and/or hub contain one or more negative spaces, the elastomer layer is molded around the parts and also in or through the negative spaces. This allows the set elastomer to be attached to the parts by bonding to itself through the negative spaces thereby creating a shape that will hold itself to the parts; rather than relying on adhesion or non-bonded methods. Also, when weight or force is applied to the disc prosthesis, the elastomer can compress into or through the negative spaces.

In embodiments where the one or more endplates contain low-friction pads, the low-friction pads are made out of a low friction biocompatible material, preferably with a coefficient of friction verses dry steel of 0.3 or less, preferably approximately of 0.1 to 0.3. Suitable commercially available biocompatible materials include, but are not limited to, ultra-high molecular weight polyethylene (UHMWPE), Teflon®, and Nylon®. The low-friction pads provide a surface that the elastomer can easily slide over when there is motion.

Additionally, the artificial joint or prosthesis device optionally comprises a keystone component that is slidably engagable with the core and the endplate, and preferably the low-friction pads, when these components are fitted together. When a second endplate is used, the artificial joint or prosthesis device optionally comprises a second keystone component that is slidably engagable with the core and the second endplate (as well as any low-friction pads). The one or more endplates and core can be inserted separately into patient and fitted together. When the one or more endplates and core are properly adjusted, the keystone component(s) is engaged with the endplate(s)-core assembly and locks these components together. Optionally, each endplate has one or more rails extending from its surface. When placed together, the core fits within these rails and is partially encased. These rails maintain proper rotational alignment of the core with relation to the endplate and limit the amount of flexion and extension and lateral bending of the device. In addition, the rails may optionally extend toward the vertebral body or bone and provide anchoring of the device to the bone.

Additionally, the artificial joint or prosthesis system optionally comprises a torus and collar system around the hub that is able to prevent or reduce displacement of the core from the endplate. In one embodiment, the surface of the hub contains a collar, i.e., a circumferential bulge around the hub having an increased diameter, that fits into a corresponding circumferential space in the endplate. In one embodiment, the torus and collar system is preferable over plane guide rims used in other prosthesis devices because the torus and collar system allows in situ insertion of the hub into the endplate without over-distraction. Plane guide rims typically require over-distraction for in situ insertion of the guide rims.

In a further embodiment, the artificial joint or prosthesis system has a system for alignment of the components for implantation within the patient's anatomy such as radio-opaque material in sufficient amounts so as to be able to provide radiographic guidance of insertion and alignment of the prosthesis system. In another embodiment, the artificial joint or prosthesis system and/or components of the artificial joint or prosthesis system are made from or contain electrically conductive material in sufficient amounts so as to be able to provide for electrical and electrophysiological guidance of insertion and alignment of the device.

In another embodiment, the present invention provides a method of treating a joint disorder comprising the step of inserting an artificial joint into a patient, wherein the artificial joint comprises:

a) a core comprising: a hub, a flange, and a biocompatible elastomer layer that encases the flange; wherein the hub comprises a rigid material able to maintain a selected prosthesis height, and a curved surface, and wherein the hub is disposed within the flange so that at least a portion of the curved surface of the hub extends above the surface of the flange; wherein the flange is a rigid component able to provide internal structural support for the elastomer layer; and b) an endplate comprising: a structural component able to engage a bone or cartilage surface at or near a joint a first low-friction surface that engages the elastomer layer, and a second low-friction surface that engages the curved surface of the hub. Preferably the structural component comprises a hollow, cylindrical mesh cage with circle, oval, or bean shaped base. In a further embodiment, the elastomer layer also encases at least a portion of the hub or the entire hub.

In another embodiment, the present invention provides a method of treating a discogenic disease or spinal disorder comprising the step of inserting an intervertebral prosthetic disc into a patient, wherein the prosthetic disc comprises:

a) a core comprising a hub, a flange, and a biocompatible elastomer layer surrounding the flange;
wherein the hub comprises a rigid material able to maintain a selected intervertebral disc height, and a curved surface having a coefficient of friction of 1 or less such as dry polished steel with itself;
wherein the hub is disposed within the flange so that the curved surface of the hub extends above the surface of the flange; wherein the flange is a rigid component able to provide internal structural support for the elastomer layer; and wherein the elastomer layer is molded around the flange and optionally at least a portion of the hub or the entire hub and has a Shore hardness of approximately 60 A to 100 A, a modulus of elasticity of approximately 0.01 GPa to 0.1 GPa, and a kinetic friction coefficient with dry steel of approximately 1 or less; and b) an endplate comprising a structural component able to engage a natural vertebral endplate, a first low-friction surface that engages the elastomer and preferably has a coefficient of friction verses dry polished steel of 0.1 to 0.3 or less such as in Ultra-High Molecular Weight Polyethylene, and a second low-friction surface that engages the hub and preferably has a coefficient of friction of approximately 1 or less such as dry polished steel with itself. Preferably the structural component comprises a hollow, cylindrical mesh cage with circle, oval, or bean shaped base able to engage a natural vertebral endplate.

Optionally, the disc prosthesis system comprises a second endplate having a structural component able to engage a second natural vertebral endplate that is preferably a hollow, cylindrical mesh cage with circle, oval, or bean shaped bases, a first low-friction surface which engages the elastomer layer, and a second low-friction surface which engages the curved surface of the hub which extends below the surface of the flange. In a further embodiment, one or both of the endplates further comprise a low-friction pad wherein the first low-friction surfaces which engages the elastomer layer are located on the surface of the low-friction pads.

In a further embodiment, this method further comprises removing an injured intervertebral disc, bone or other material from the patient prior to inserting the intervertebral prosthetic disc. In one embodiment, the prosthesis is circular, elliptical, or bean shaped as in an axial view of a vertebral body, and is inserted anterior to posterior. In another embodiment, the prosthesis is bean shaped or crescent shaped and is inserted into the patient using the transforaminal approach. In another embodiment, the prosthesis is elongated for direct lateral insertion.

In one embodiment, the present invention provides an artificial limb, such as an artificial arm or leg, which contains one or more artificial joints as described herein. In another embodiment, the present invention provides a robotic or mechanical arm or appendage having an artificial joint as described herein.

DETAILED DESCRIPTION OF THE INVENTION

Figure 1:
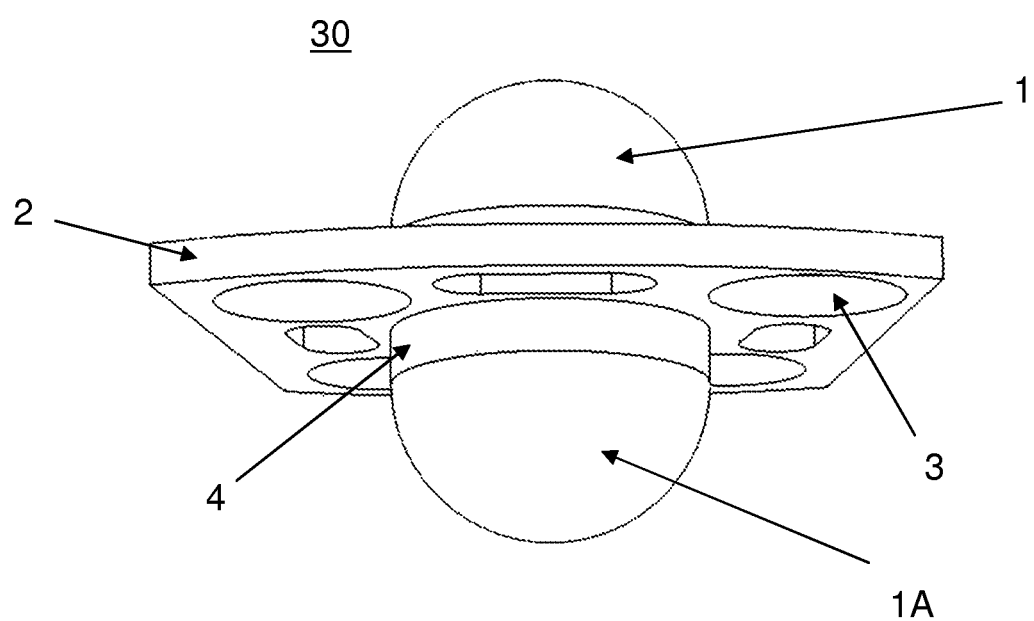
FIG. 1 shows a hub and flange of the inner core of an artificial joint or prosthesis system in one embodiment of the present invention. The elastomer layer is not shown in this figure.

Degenerative changes in the intervertebral discs of the human spine can cause pain, numbness, tingling, and weakness of the neck, back, arms, and legs. The current standard for treating degenerative disc disease and other spinal disorders is a decompression and fusion. Unfortunately, spinal fusions disrupt the natural bio-mechanics of the spine by eliminating motion at the fusion site and increase the strain on the remaining motion segments of the spine. Similar to joint replacement surgery, artificial prostheses can be implanted into the patient as an alternative to spinal fusion.

The present invention provides motion-preserving artificial joints and prosthesis systems which can be used as intervertebral prosthetics and prosthetic joints. The artificial joints and prostheses of the present invention comprise a core having a hub, a flange, and a biocompatible elastomer layer surrounding the flange to serve as a shock absorbing material. The artificial joints and prosthesis systems as a whole and their individual components can be contoured or shaped to fit with an intervertebral space or within ball-and-socket, hinged, and fixed joint anatomies.

Hinge joints provide flexion and extension and include but are not limited to the human elbow and knee. Arthroplasty of the knee involves the implantation of a curved prosthesis to the femur such as the femoral endplate of the present prosthetics. An endplate is attached to the tibia that has a surface for the femoral implant to slide and rotate with. The present elastomeric prosthesis system can be applied to hinge joints by using a circular hub and flange to form a hinge joint. The hub components can optionally be j-shape to resemble the curvature of a natural femoral head. The tibial articulation surface prosthetic can be made of ultra high molecular weight polyethylene for low-friction and biocompatibility.

Ball-and-socket joints allow orbital rotation and include but are not limited to joints such as in the human hip and shoulder. Hip arthroplasty surgery involves the replacement of the femoral head with a ball prosthesis such as a hub of the present invention. An embodiment of the present invention uses a conical flange, elastomer, and pad for shock absorption. An articulation surface is implanted in the acetabulum. Similar to knee and disc arthroplasty, the hub can be entirely or partially encased with biocompatible elastomer by using negative spaces to allow a continuous cast of elastomer so that the shape of the set elastomer holds it to the hub, and the acetabular prosthetic can be made of ultra high molecular weight polyethylene as described for the low-friction pad described below.

Fixed joints include joints that are found in but are not limited to the human cranium. Fixed joints allow for the shifting of the plates of bones that surround and protect the brain. Craniotomy procedures often involve the removing of a window of cranial bone to access the anatomy. These procedures are often completed by affixing the removed bone back into the skull or implanting a prosthetic plate. The present invention can be applied to fixed joint anatomies by casting elastomer around the edges of plate prosthetics using a flange to provide translational shock absorption upon the shifting of the plates of the cranium.

Figure 2:
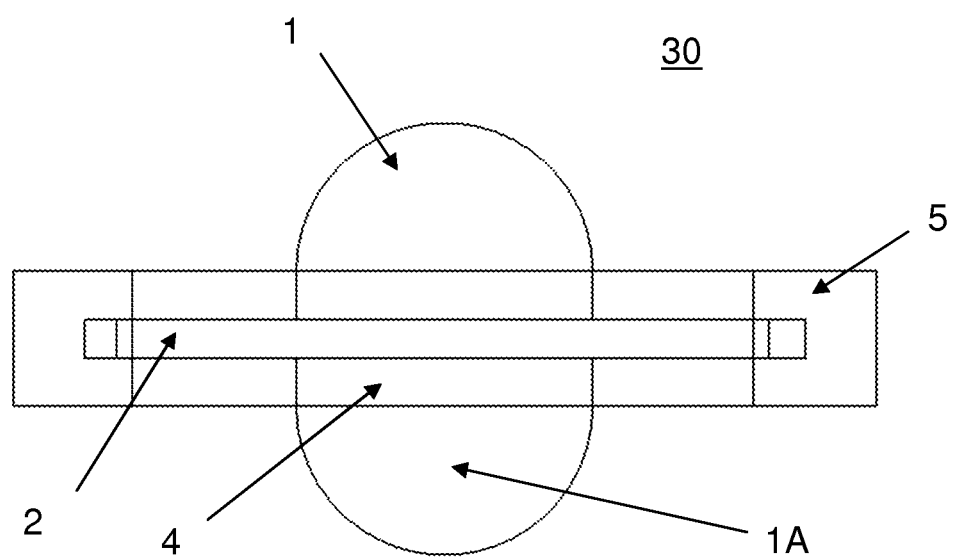
FIG. 2 shows a cross-sectional view of the core including the elastomer layer in one embodiment of the invention.

FIG. 1 shows a core 30 of an artificial joint or prosthesis device of the present invention without the elastomer layer. A hub 4 having a first curved surface 1 and a second curved surface 1A is positioned within a flange 2. The hub 4 and flange 2 are made out of a rigid biocompatible material that is suitable for insertion into the human body. Preferably, the hub 4 and flange 2 are constructed from a rigid biocompatible material such as titanium alloys, stainless steel, or polyether ether keytone (PEEK). The flange contains a plurality of negative spaces 3 that allow an elastomer layer 5 to be molded around and through the flange 2. As shown in FIG. 2, the elastomer layer 5 encompasses the top and bottom surfaces of the flange 2. A portion of the hub 4, or the entire hub 4, may also be incased by the elastomer and may also have negative space to allow the shape of the set elastomer layer 5 to hold itself to the hub 4. The continuous mold of elastomer around and through the flange 2 attaches the elastomer layer 5 to the flange 2 and hub 4. In this way, the hub 4, flange 2, and elastomer layer 5 can become a single motion component.

The elastomer is a biocompatible material able to provide the artificial joint or prosthetic device with shock absorption. Such biocompatible materials include, but are not limited to, polyurethane, polyethylene, and silicone. Preferably the elastomer is polyurethane. Commercially available biocompatible elastomers that can be used in the device include, but are not limited to, Biomer® Elast-Eon™, and Monothane®.

Figure 3A:
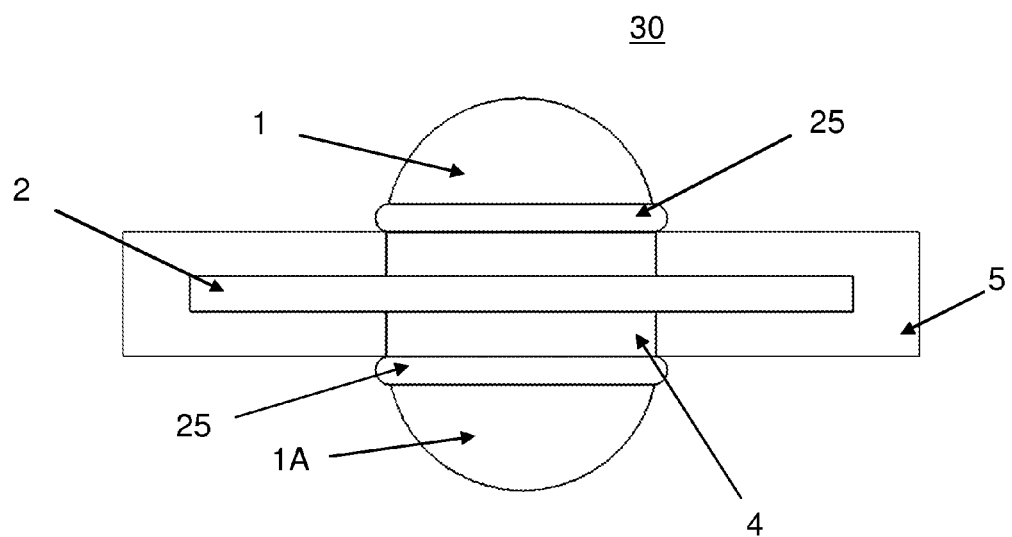
FIG. 3A shows a cross-sectional view of a core which further comprises a collar formed on the surface of the hub in order to prevent displacement of the hub when mated with the endplate.

FIG. 3A shows a core 30 of an artificial joint or prosthesis device of the present invention having a first curved surface 1 extending above the surface of the flange 2 and a second curved surface 1A extending below the surface of the flange 2. The hub 4 can have a collar 25 above and/or below the elastomer layer 5 to provide an additional surface to secure the core 30 to the endplate 13 (shown in FIG. 10).

Figure 3B:
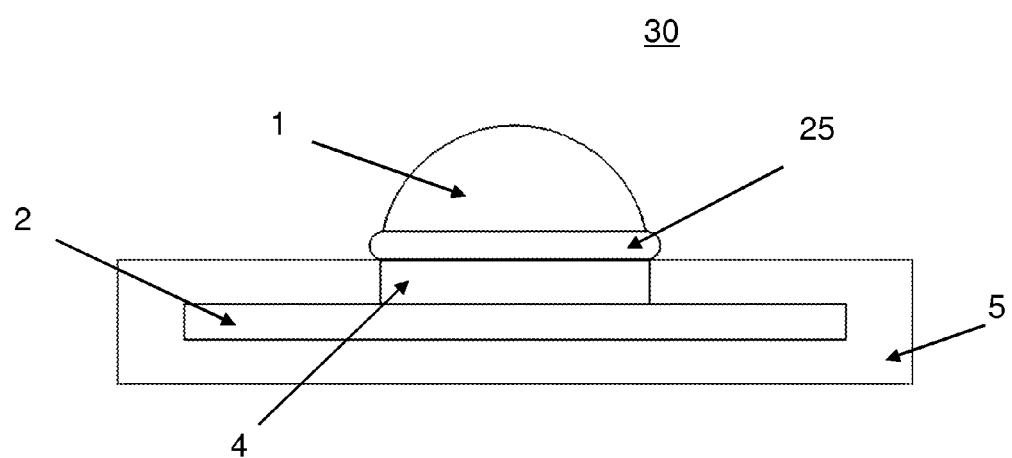
FIG. 3B shows a cross-sectional view of a core having a single curved surface that extends above the flange. The lower side of the core is fully surrounded by the elastomer layer for increased shock-absorption and increased surface area of elastomer.

In the embodiment illustrated in FIG. 3B, the hub 4 contains a single curved surface 1 which extends above the flange 2. The side of the core 30 that does not contain the curved surface 1 engages a flat endplate (not shown) or contains one or surface attachments (not shown) that can attach to a bone or cartilage surface. This embodiment may or may not use a keystone (shown in FIGS. 11 and 12) to secure the core 30 to an endplate 13.

Figure 4:
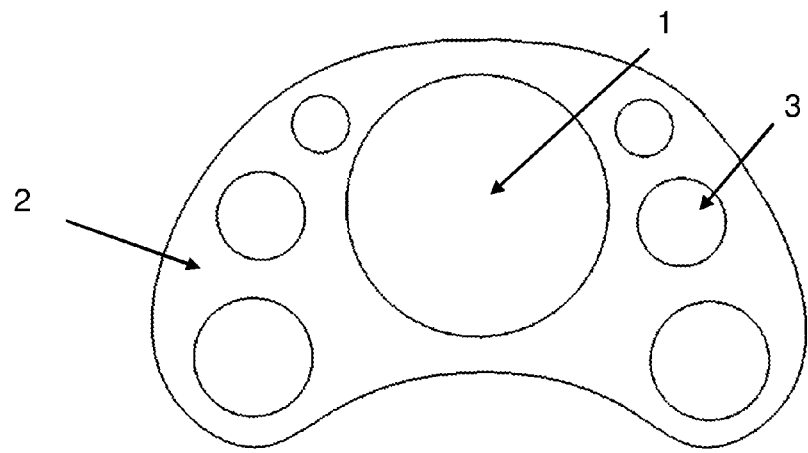
FIG. 4 shows a hub and flange of a prosthesis that is bean-shaped and more closely matches the shape of a natural intervertebral disc.
Figure 5:
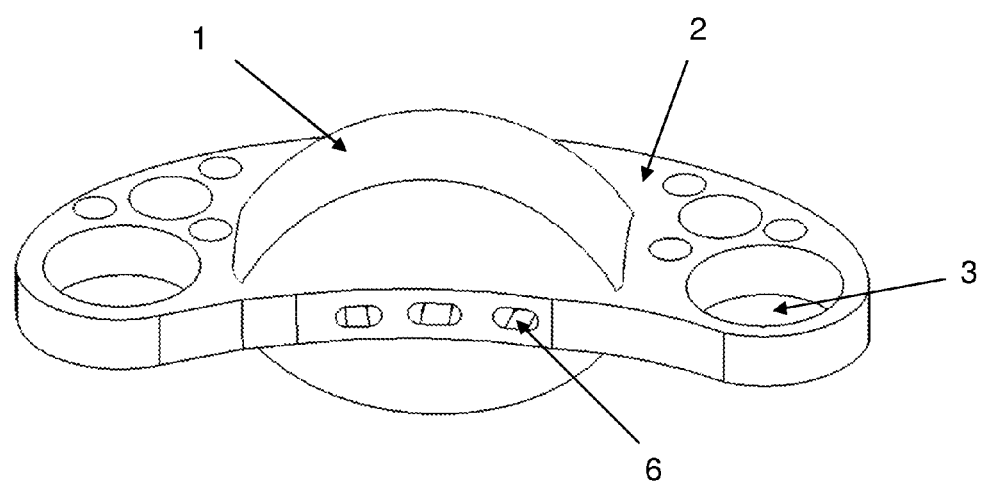
FIG. 5 shows a crescent-shaped prosthesis that is elongated along an arc that allows for easier implantation into an intervertebral space using the transforaminal approach.

A prosthetic disc system does not have to be circular, but instead can be "bean shaped" or "crescent shaped" as shown in FIGS. 4 and 5. Such a prosthetic disc system is similar to the shape of a natural intervertebral disc and is similar to the shape of a natural vertebral body. While only the core 30 is shown in FIGS. 4 and 5, this embodiment also has bean shaped endplates (not shown). A crescent shaped implant improves the ease of implantation of the prosthesis into the intervertebral space using the transforaminal approach. It is also possible to elongate and configure the device to the shape and size that is preferable for direct lateral insertion into the intervertebral space.

FIG. 5 also discloses longitudinal negative spaces 6 within the flange 2 to allow the elastomeric layer 5 to cast itself into the flange 2 in another axis other than in negative spaces 3 and may extend through the entire device to enable to elastomer to bond to itself, or may extend only partially through the device so that the set elastomer forms a peg shape. Optionally, hub 4 and curved surface 1 (as shown in FIG. 1) may also contain negative spaces to provide for a portion of hub, or the entire hub to be encased with elastomer 5.

Figure 6:
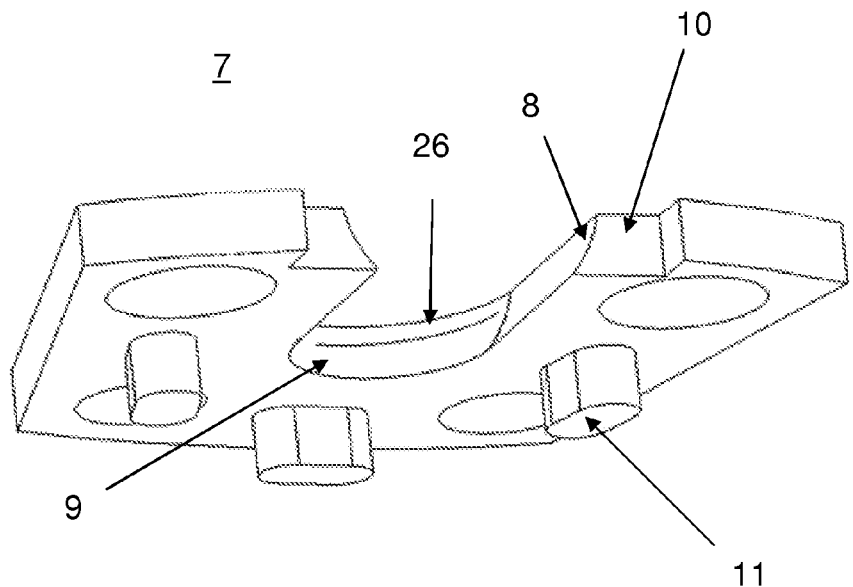
FIG. 6 shows a low-friction pad which can be part of the endplate in one embodiment of the invention.
Figure 7:
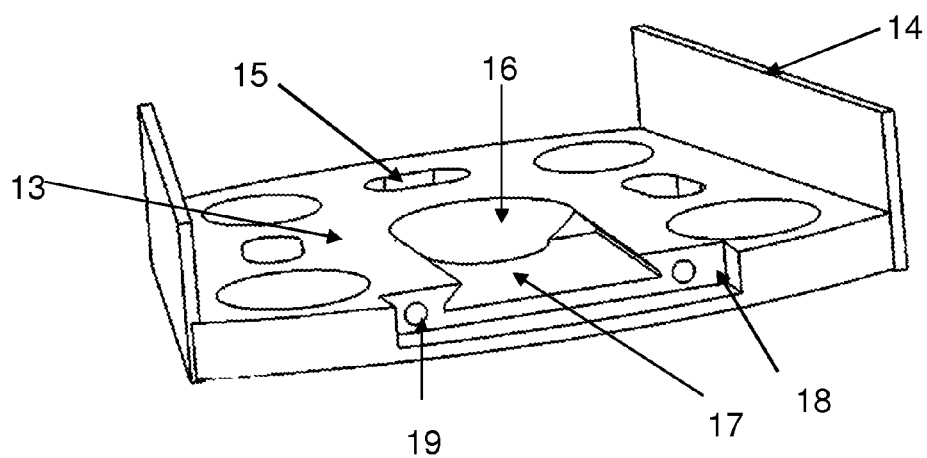
FIG. 7 shows an endplate in one embodiment of the invention.
Figure 10:
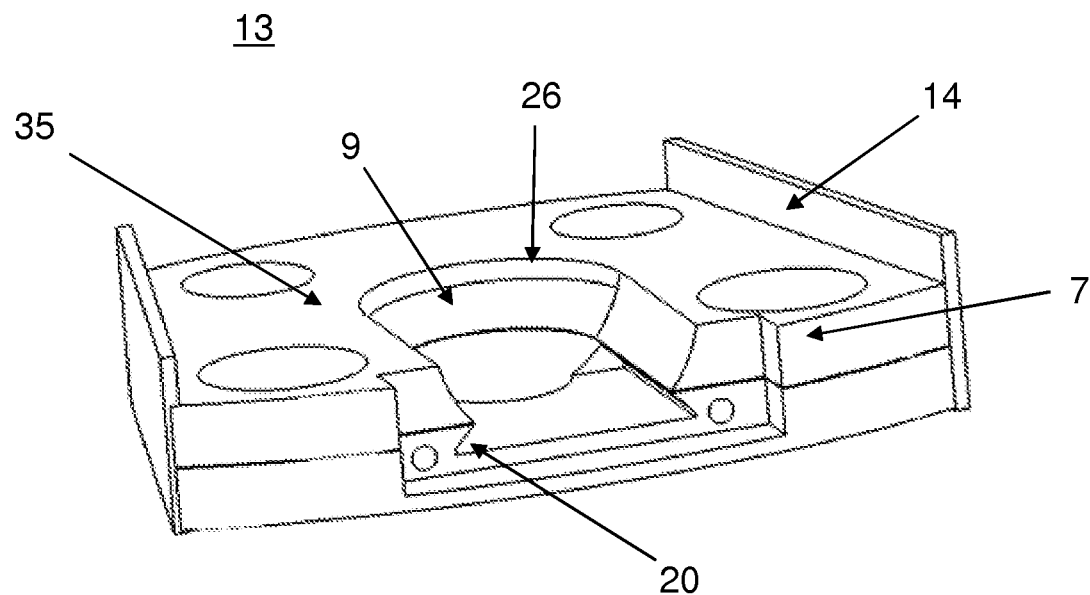
FIG. 10 shows the low-friction pad assembled together with the endplate in one embodiment of the invention.

FIG. 6 shows a low-friction pad 7 which can be part of the endplate 13 (shown in FIGS. 7 and 10). The low-friction pad 7 is made out of a low friction biocompatible material with preferably a coefficient of friction verses dry steel of 0.3 or less. One such commercially available biocompatible material is ultra-high molecular weight polyethylene (UHMWPE) and provides a surface for the elastomer layer 5 to slide long with as the vertebral column or joint moves. Other commercially available materials that are suitable include, but are not limited to Teflon® or Nylon®. Pegs 11 extend from the lower surface of the low-friction pad 7 and attach pad 7 to the endplate 13 by engaging slots 15 in the endplate 13.

In one embodiment of the invention, an endplate 13 having a low-friction pad 7 is inserted into the patient first and the core 30 is assembled in situ by inserting the core 30 into the endplate 13 through slot 8 of the pad 7. In this embodiment, there is shoulder 10 that allows the keystone 21 (shown in FIG. 11) to be pressed against the pad 7 and core 30 thereby securing the core 30 and endplate 13 together. Shoulder 10 may also have threaded holes (not shown) to allow the keystone 21 to be screwed into the pad 7. The pad 7 has a concave surface 9 that provides a surface for the hub 4 to articulate.

Figure 8:
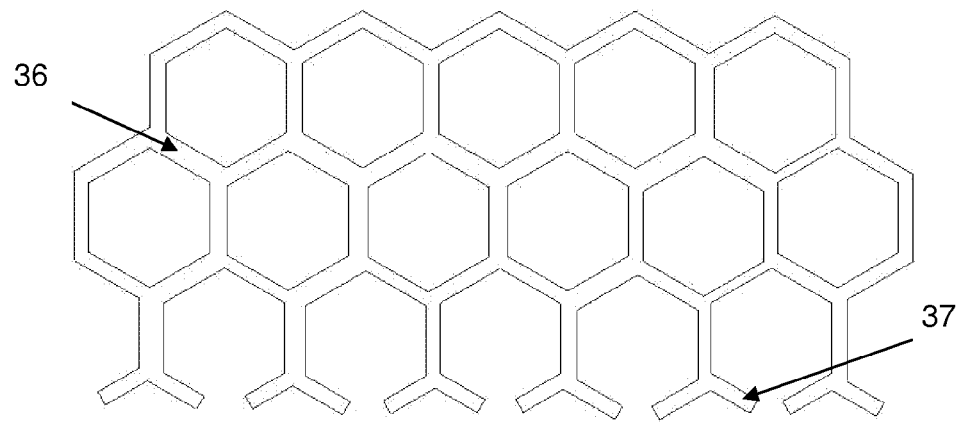
FIG. 8 shows a mesh material which can be used to form the structural component or anchor in one embodiment of the invention. The mesh material can be formed into structures such as rings and cones.

The endplate 13, as illustrated in FIG. 7, is made of a rigid biocompatible material such as titanium alloys, stainless steel, or polyether ether keytone (PEEK). The endplate 13 attaches to the natural vertebral endplate using structural component 38 (shown in FIG. 9). Preferably, the structural component is made from a mesh cage material as illustrated in FIG. 8 to allow for bone growth through the negative spaces in the mesh. Structural component 38 can also be screws, anchors, keels, spikes, pegs, teeth, prongs, ridges or similar structures as known in the art. The pegs 11 of low-friction pad 7 fit into slots 15 of the endplate 13 to hold the pad 7 and the rest of the endplate 13 together. Second low-friction surface 16 engages the curved surface 1 of hub 4 and provides a surface for the hub 4 to articulate with the movement of a patient's body. As shown in FIG. 7, the second low friction surface 16 may be concave.

The endplate 13 may have rails 14 or other structural elements that maintain alignment of the core 30 with the endplate 13. In one embodiment, the rails 14 are constructed as a single piece with the rest of the endplate 13. In another embodiment, the rails 14 attach and detach from the rest of the endplate 13 for in situ or ex situ assembly of the prosthetic device. In another embodiment (not shown) the alignment of the core 30 and endplate 13 is a motion limiter of hub 4 which prevents over-rotation and ensures proper alignment between the components of the prosthetic device. Additionally, rails 14 may extend toward the vertebral endplate to secure the device to the bone.

As shown in FIG. 7, the endplate 13 may comprise a lateral slot 17 which has a slightly shallower depth than the second low-friction surface 16 so that when the core 30 is assembled in situ with the endplate 13, the hub 4 snaps into proper engagement with the second low-friction surface 16 while under compressive forces from the patient's body, particularly the spine. In another embodiment, slot 17 has the same depth of concavity as second low-friction surface 16 for smooth insertion of the hub 4. Lower shoulder 18 aligns with shoulder 10 to present a substantially uniform surface when the low-friction pad 7 is assembled with the rest of the endplate 13. The surface formed by shoulders 10 and 18 allows the keystone 21 to be flush with the pad 7 and the rest of the endplate 13 when installed. Optionally, the endplate 13 contains threaded hole 19 which aligns with hole 24 of the keystone 21 and provides a space for a screw to secure the keystone 21 and endplate 13 together.

The artificial joint or prosthesis is affixed to the vertebral body using screws, anchors, keels, spikes, pegs, teeth, prongs, ridges or similar structures. FIG. 8 illustrates a sheet of mesh 36 that can be used as a vertebral endplate anchor. The mesh can be made of titanium alloys, stainless steel, or polyether ether keytone. In the shown embodiment, the mesh is hexagonal. Other embodiments are pentagonal, diagonal or other shapes. The mesh cage has or can be cut to have protrusions 37 that assist in securing the device to the vertebral endplate. This embodiment uses the surface area of the endplate prosthesis to prevent the cage from subsiding deeper than desired into the bone or the vertebral body. Another embodiment (not shown) uses a cap or a blunt edge that engages the vertebral endplate and secures the device by the shape of the anchor with the concavity of the natural vertebral endplate.

Figure 9:
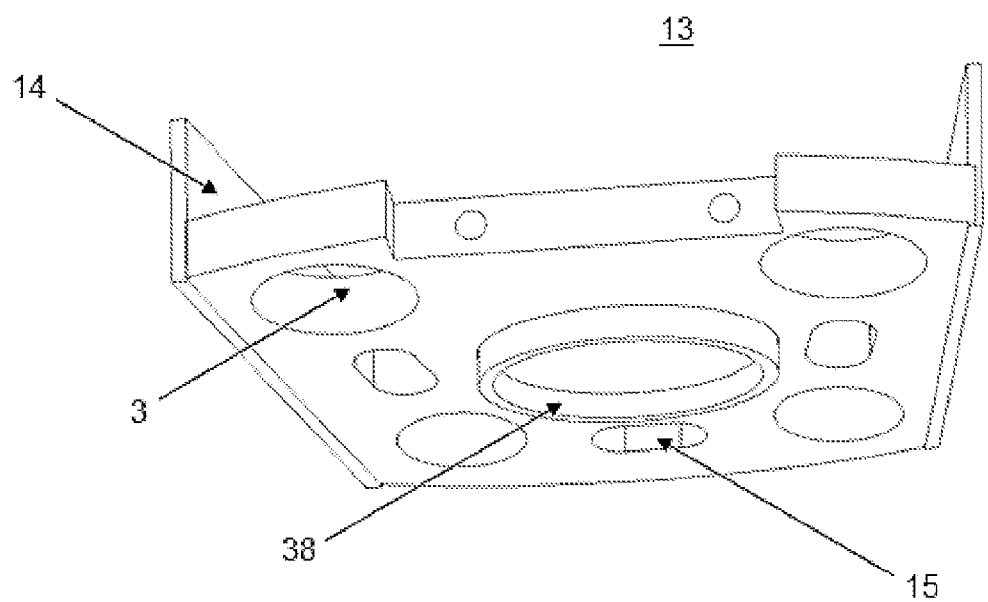
FIG. 9 shows an endplate in one embodiment of the invention with a circular anchor that is able to engage a vertebral endplate.

The mesh cage is preferably formed into a cylindrical base as shown in FIG. 9, so that it fits within the concavity of a natural vertebral body; however, other base shapes such as oval or bean-shaped bases are also available. A hollow cylinder as shown in FIG. 9 is preferable so that it has a space that can contain bone graft, bone morphogenic protein, or other material. The mesh 36 contains negative spaces to allow bone growth through the prosthetic anchor. Optionally, the structural component 38 can be as sized and implanted separately within the concavity of the natural vertebral end plate then assembled to the endplate prosthesis in situ so that the device can be implanted with minimal distraction of the anatomy.

In addition, surface coatings such as hydroxyapatite may be used instead, or in conjunction with affixation structures. Also, porous surfaces and negative spaces may be used for bone incorporation of the endplate prosthesis. Osteoconductive, osteoinductive, and osteogenic material may also be used to affix the prosthetic to the spine.

In one embodiment, the core 30 and endplate are assembled in situ and insertion of the hub 4 through slots 8 and 17 is secured in place with a keystone 21 that secures the hub 4, pad 7 and rest of the endplate 13 together. Alternatively, the components are assembled ex situ prior to implantation.

Figure 11:
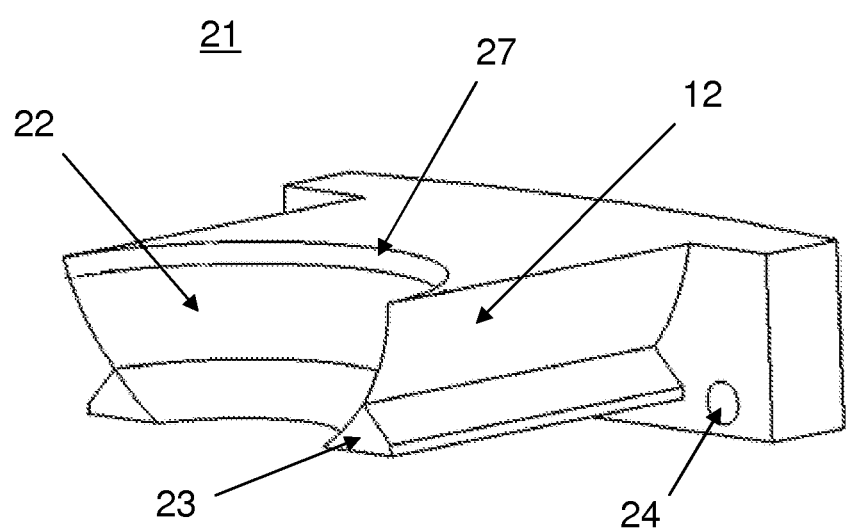
FIG. 11 shows a keystone that is able to secure an assembled core and endplate together.

FIG. 10 shows an assembled endplate 13 containing a low-friction pad 7. Optionally, the endplate 13 forms a guide slot 20. As shown in FIG. 11, the keystone 21 can contain a corresponding guide rail 23 which engages guide slot 20 when the keystone 21 is inserted into the endplate 13. When inserted, the side surface 12 of the keystone 21 contacts the side of slot 8 and the keystone 21 secures the low-friction pad 7 to the rest of the endplate 13 and the core 30 to the endplate 13. Hole 24 of the keystone 21 aligns with threaded hole 19 of the endplate 13 and may be threaded to allow a screw to secure the keystone 21 and endplate 13 together. The keystone 21 may also have holes to allow the keystone 21 to be screwed into the low-friction pad 7.

Concave surface 22 joins with lateral concave surface 9 to form a space for the curved surface 1 of the hub 4 to move with movement of the spine. Concave surface 22 may have a partial negative space torus 27 that engages collar 25 of the hub 4 as shown in FIGS. 3A and 3B to prevent displacement. Lateral concave surface 9 may also have a partial negative space torus 26 that engages torus 25 to secure the hub 1 and prevent displacement. The partial negative space torus 26, mates with partial negative space torus 27 to form a complete negative space torus that engages collar 25 to prevent displacement of the hub 4. Optionally, the negative space tori at 26 and 27 are sized slightly larger than collar 25 to prevent displacement of the hub while still allowing movement of the core to move with movement of the spine. Also optionally, the displacement torus may contain a rotational limiter to provide rotational alignment of the core and the endplate. In one embodiment, collar 25 may have a portion or multiple portions with a greater radius than the rest of the collar and engages corresponding greater radius torus space 27 of the endplate 13 and the keystone 21. By limiting the arc of the deeper torus space, the device will be able to limit the amount of rotational movement of the device and maintain alignment of the core and the endplate. The preferred maximum rotation limit of the intervertebral device is approximately 90 degrees.

Figure 12:
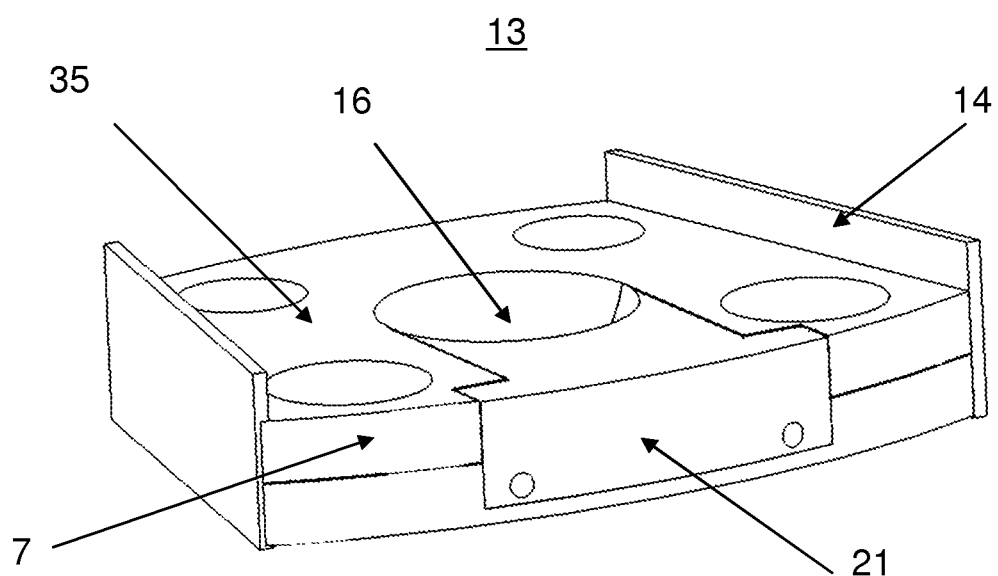
FIG. 12 shows the keystone of FIG. 11 inserted into the low-friction pad/endplate assembly of FIG. 10.

An assembled endplate 13 with an inserted keystone 21 is illustrated in FIG. 12. Rail 14 has a height above the low-friction pad 7 to maintain alignment of the core 30 with the endplate 13. When a core 30 is assembled with the endplate 13, the first low-friction surface 35 contacts the elastomer layer 5.

In one embodiment, the depth and concavity of the combined surfaces 9 and 22 have the same arc and height as hub 4. In other embodiments, the depth and concavity of the combined surfaces 9 and 22 and height of hub 4 are adjusted to control the friction between the elastomer layer 5 and the first low-friction surface 35 of the endplate 13. A shallower depth of concavity may create a space between the elastomer layer 5 and the endplate 13 and less friction. In increased depth may cause compression of the elastomer layer 5 and increased friction. Similarly, an increased height of the hub 4 may create a space between the elastomer layer and the first low-friction surface 35 of the endplate 13 and less friction. A decreased height of the hub 4 may cause compression of the elastomer layer 5 and increased friction. In another embodiment, a decreased radius arc of hub 4 with respect to surfaces 9 and 22 may be used for increased translational freedom.

The embodiment depicted in FIG. 12 is a preferred configuration of the endplate 13 of a prosthetic disc for use with insertion of the prosthetic into the intervertebral space using the anterior approach. The endplate and rails 14 are trapezoidal for insertion alignment and maintaining rotational alignment of the core 30 with the endplate 13. Other preferable embodiments for insertion using an anterior approach have circular or oval shaped prosthetics.

Figure 13:
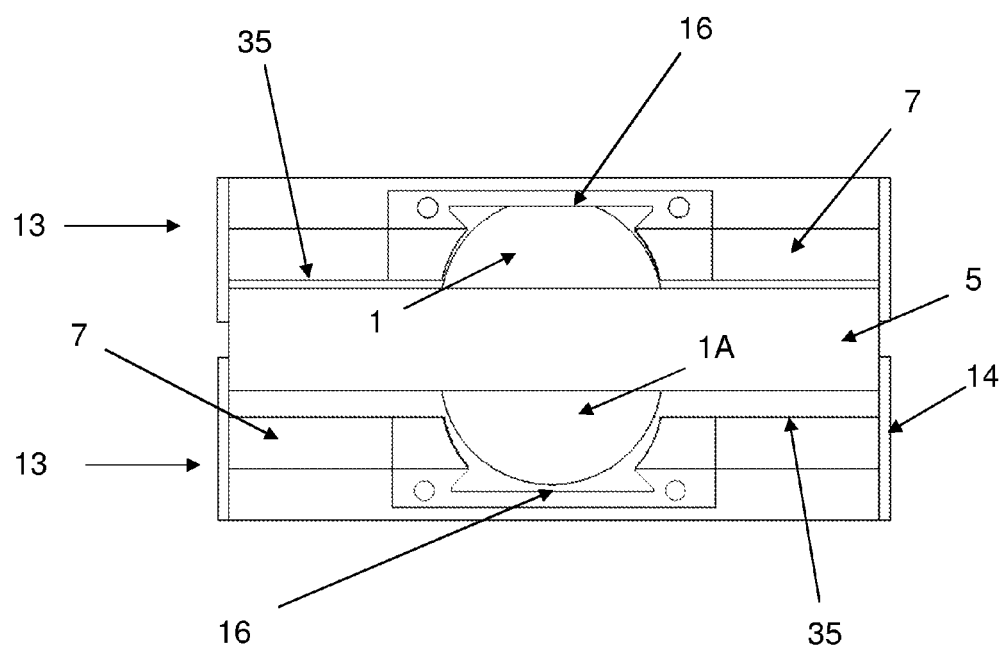
FIG. 13 shows a top view (with respect to a supine patient) of an assembled prosthesis system having a first and second endplate in one embodiment of the invention.

FIG. 13 shows a top view of an assembled prosthesis system when implanted from the anterior approach of the spine having a first and second endplate 13. Both endplates 13 contain a low-friction pad 7 wherein the core 30 is inserted in between the low-friction pads 7. The height of the hub 4 or depth of the curved surface of the endplates 13 may be adjusted to allow space between the elastomer layer 5 and the pad 7 at a neural position, or allow compression of the elastomer layer 5 at a neutral position. Rails 14 partially encase the core and are shorter than half of the height of the core 30 with the pads 7 in place to allow for compression of the elastomer layer 5. Preferably, the height of the rails will allow flexion and extension of the spine, but limit flexion and extension to approximately 60 degrees. The height of the rails also allows for lateral bending of the spine, but limit lateral bending to approximately 45 degrees. The rails 14 may extend toward the vertebral endplate to provide anchoring of the device to the bone.

In one embodiment, endplates that are flat, and do not have concave surfaces to engage the 4 hub, also do not have slots 8 and 17 for installation of the hub 4. This embodiment may or may not use a keystone 21 to secure the endplates and may only be secured by the pegs 11 of the low-friction pads inserted into slots 15.

The preferred dimensions of the assembled disc prosthesis system are modeled to fit within the natural intervertebral disc spaces of the human spine with a height of approximately 5 mm to 20 mm, an anterior-posterior dimension of approximately 5 mm to 50 mm, and a lateral dimension of approximately 5 mm to 80 mm.

In one embodiment, the diameter of the curvature of surfaces 9 and 22 and the diameter of hub 4 is approximately 5 mm to 60 mm similar to the concavity of that of the natural spine. In another embodiment of the invention, the curvature of the concavity is modeled to resemble more of the bean shape of the human vertebral endplates rather than a simple arc shape and uses a congruently bean shape hub 4 (not shown).

The anterior height of the prosthesis may be the same or a different height as the posterior height of the prosthesis so that the endplates are 0 degrees to 20 degrees to fit different degrees of lordosis of the natural spine.

Figure 14:
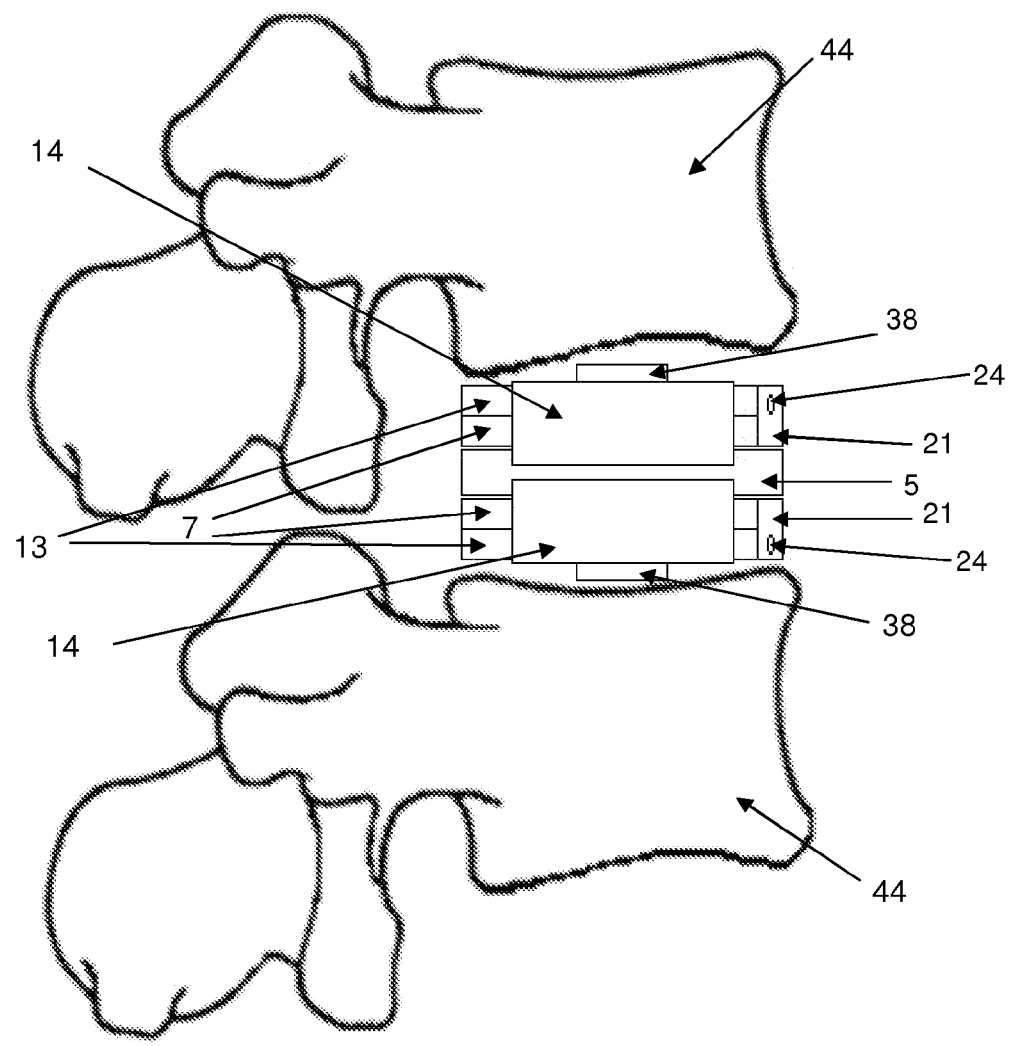
FIG. 14 illustrates a lateral view of a disc prosthesis system inserted into the intervertebral space of the spine. In this embodiment, the device engages with vertebral endplates. The flange and elastomer are planar, similar to the shape of a washer.

FIG. 14. Illustrates a disc prosthesis device of the present invention implanted in the disc space in between vertebral bodies 44. Structural components 38 have an improved fit than previous inventions because they fit within the concavity of the natural vertebral endplate. This embodiment has the keystone 21 is aligned anteriorly with the anatomy for an anterior spinal approach.

Figure 15:
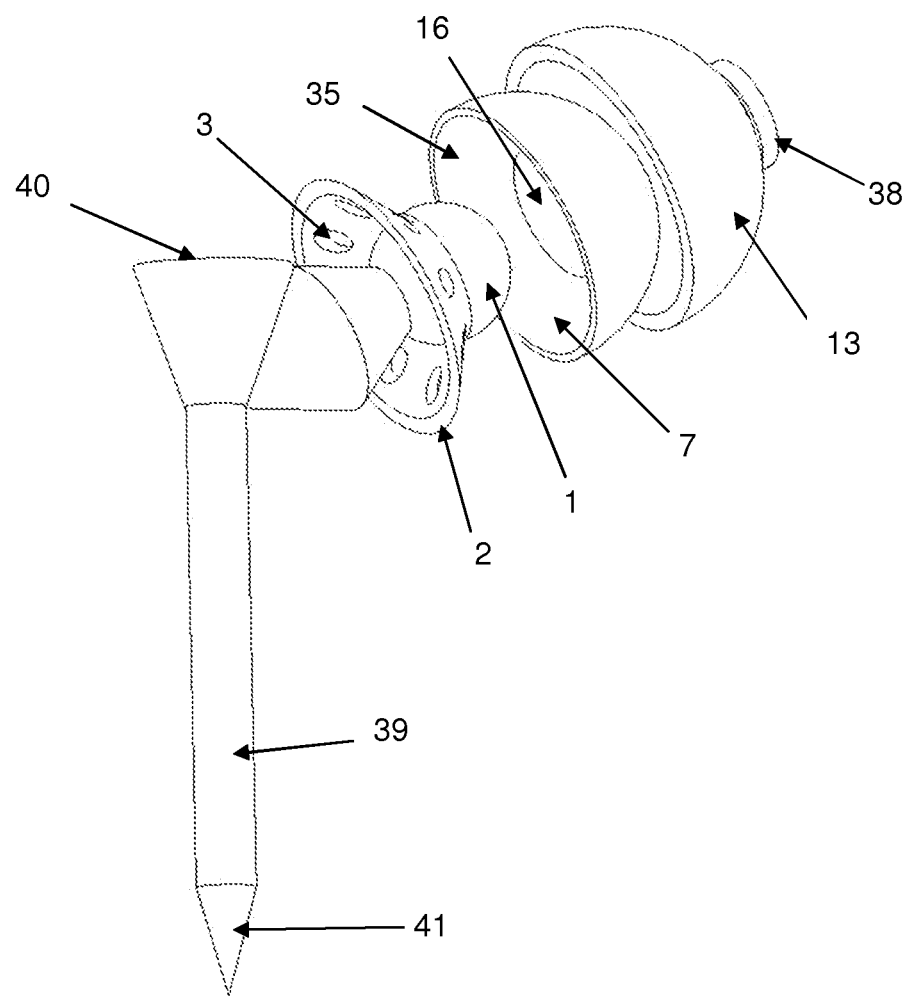
FIG. 15 illustrates an artificial joint for insertion in a hip joint. The elastomer is not shown to illustrate the flange component.

FIG. 15 illustrates an artificial joint prosthesis configured for ball-joint replacement, such as hip and shoulder arthroplasty. The hip replacement embodiment has an anchor 39 that implants within the femoral bone as commonly used in hip replacements. The anchor 39 has a conical tip 41 for ease of insertion within a reamed femur. This embodiment of the femoral stem also has a conical head that has a flat surface 40 that is a surface for tamping the implant into the femur. The flange 2 in this embodiment is conical and has a conical elastomeric layer (not shown) that engages a conical first low-friction surface 35. The curved surface 1 is spherical and the second low friction surface 16 of the endplate 13 is concave to allow orbital movement of the prosthesis. The endplate 13 in this embodiment is a cup shaped, which is preferable for acetabular implantation. The hip prosthesis may also use a mesh cage tube 38 to anchor the endplate to the bone.

Figure 16:
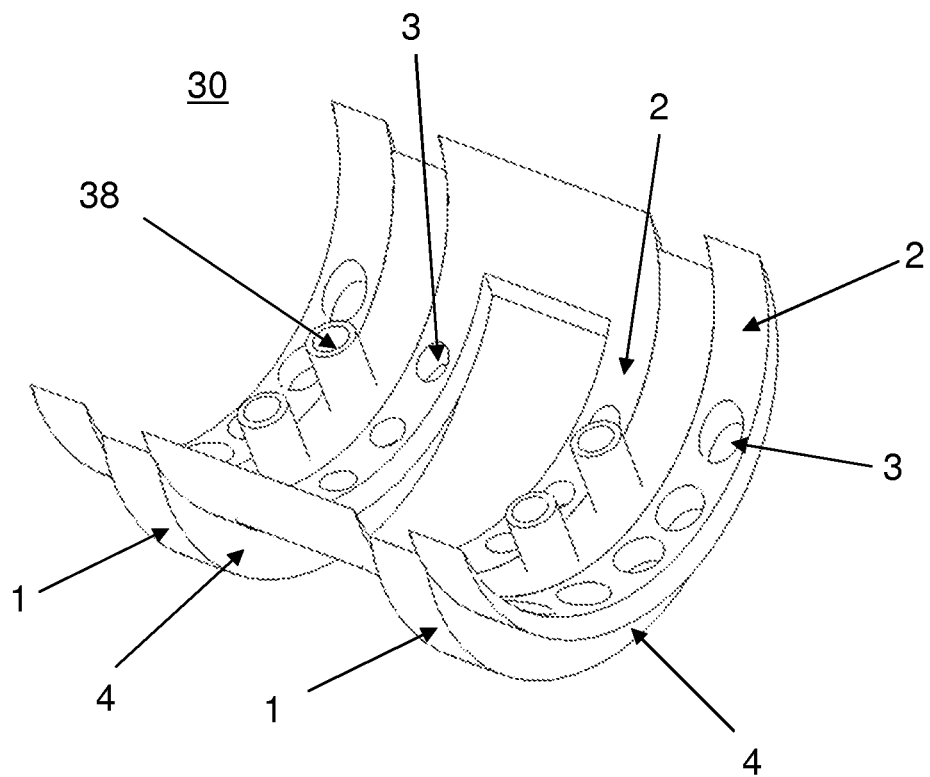
FIG. 16 illustrates an embodiment where the core is configured to form a hinge joint, such as the human knee joint.

FIG. 16 illustrates a core 30 for use in an artificial joint for the replacement of a human knee. The core 30 as shown in FIG. 16 contains two hubs 4, each containing a curved surface 1 able to contact the endplate (not shown); however, the core 30 could also contain a single hub 4 and curved surface. The articulating hubs 4 are curved and rotate along a single rotating axis, rather than orbital articulation as in other embodiments of the device. The core 30 is similar with all other embodiments of the device in that has a flange 2 that is a rigid internal structure for an elastomer layer (not shown). The flange 2 in this embodiment is curved so as to fit within a knee or elbow joint. This embodiment also has negative spaces 3 that allow a continuous cast of elastomer through the flange 2. The device is secured to a surgically prepared femoral head using mesh cage tube 38.

Figure 17:
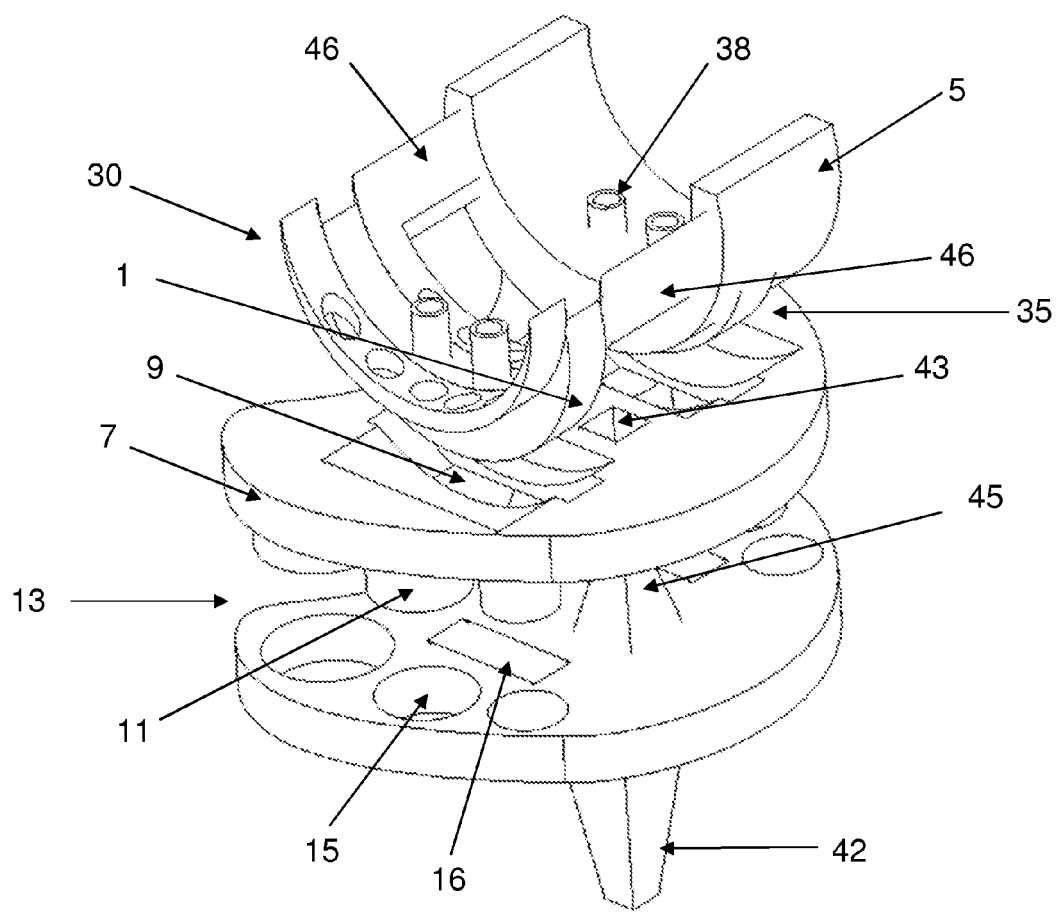
FIG. 17 illustrates an artificial hinge joint system for the replacement of a human knee. The elastomer is shown on one side of the device and not shown on the other side of the device to illustrate the flange component.

FIG. 17 illustrates a disassembled artificial joint that is configured for hinge joint replacement, such as knee and elbow arthroplasty, using the core 30 of FIG. 16. The curved surface 1 engages with the second low friction surface 16 of the endplate 13. Lateral surface 9 forms a space for curved surface 1 to articulate along a single axis of rotation similar to a door hinge. The low-friction pad 7 has a first low friction surface 35 which contacts the elastomer layer 5 (partially shown). The pad 7 may have pegs 11 to engage slot 15 to attach the pad to the rest of the rigid endplate 13. The endplate 13 may have a displacement device similar to the torus and collar system of other embodiments described herein. In the present hinge embodiment, pyramidal protrusion 45 extends through slot 43 and is a motion limiter when engaged to cross bars 46 of the core 30. The distance between cross bars 46 preferably limits the device rotation from 0 degrees of extension to 135 degrees of flexion such as that of the normal range of motion of a human knee joint. The endplate 13 of this embodiment is shaped similar to a surgically prepared tibial head of a knee joint. Pyramidal protrusion 42 is an anchor device that secures the artificial joint to the tibia. Optionally, the core 30 component may be j-shaped (not shown) rather than an arc of a circle to allow motion more similar to the curved shape of a natural femoral head.

The artificial joints of the present invention may be configured for industrial applications wherein the joint is incorporated into a robotic appendage having movement similar to that of human anatomy, such as artificial limbs or robotics used in automated surgery or automotive assembly. In robotic embodiments, the components may be made of industrial materials that may not be bio-compatible. The structural components may be galvanized steel, iron, or other metals commonly used in industry. In addition to polyethylene, Teflon® and Nylon®, the pad can be constructed of other low-friction materials used in industry such as, polypropylene and polyvinyl chloride. The elastomer may be made of commercially available polyurethane such as those used in industrial wheels and bushings.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The invention claimed is:

1. A motion-preserving artificial joint comprising:
  a) a core comprising: a hub, a flange, and a biocompatible elastomer layer surrounding the flange,
    wherein the hub comprises a rigid material able to maintain a selected height, and a curved surface, and wherein the hub is disposed within the flange so that at least a portion of the curved surface of the hub extends above the surface of the flange;
    wherein said flange is a rigid component able to provide internal structural support for the elastomer layer, and said elastomer layer has a Shore hardness of approximately 60 A to 100 A, a modulus of elasticity of approximately 0.01 GPa to 0.1 GPa, and a coefficient of friction with dry polished steel of 1 or less;
  b) an endplate comprising: a structural component able to engage a surface, a first low-friction surface that engages the elastomer layer, and a second low-friction surface that engages the curved surface of the hub; and
  c) a torus collar on the surface of the hub and a corresponding negative space torus in the surface of the second low-friction surface, wherein said collar is able to be positioned into said negative space torus and reduce displacement of the core from the endplate and maintain and limit rotation of the components to approximately 90 degrees.

2. The artificial joint of claim 1 further comprising a keystone component that is slidably engagable with the core and endplate, and wherein said keystone component locks the core and endplate together when engaged.

3. The artificial joint of claim 1 further comprising one or more rails extending from the endplate and at least partially encasing the core, wherein said one or more rails are able to limit the amount of flexion and extension of the device to 60 degrees and lateral bending to 45 degrees.

4. The artificial joint of claim 1 wherein the structural component comprises a hollow and cylindrical mesh cage.

5. The artificial joint of claim 1 wherein the core and endplate are crescent shaped appropriate for implantation between vertebral bodies.

6. The artificial joint of claim 1 wherein said flange contains one or more negative spaces and said elastomer layer is molded around said flange and through said one or more negative spaces.

7. The artificial joint of claim 1 wherein the endplate further comprises a low-friction pad wherein the first low-friction surface which engages the elastomer layer is located on the surface of the low-friction pad.

8. The artificial joint of claim 7 wherein the low-friction pad has a coefficient of friction with dry polished steel of 0.3 or less.

9. The artificial joint of claim 1 wherein the curved surface of the hub has a coefficient of friction with dry polished steel of 1 or less.

10. The artificial joint of claim 1 wherein components of said artificial joint are able to be reconfigured for insertion between endplate, ball-and-socket, hinge, and fixed joint anatomies.

11. A method of treating a discogenic disease, a spinal disorder, or a joint disorder, comprising the step of inserting an intervertebral prosthesis or artificial joint prosthesis into a patient, wherein said prosthesis comprises:
  a) a core comprising a hub, a flange, and a biocompatible elastomer layer surrounding the flange,
    wherein the hub comprises a rigid material able to maintain a selected intervertebral disc height, and a curved surface, and wherein the hub is disposed within the flange so that the curved surface of the hub extends above the surface of the flange, and
    wherein said flange is a rigid component able to provide internal structural support for the elastomer layer, and said elastomer layer has a Shore hardness of approximately 60 A to 100 A, a modulus of elasticity of approximately 0.01 GPa to 0.1 GPa, and a coefficient of friction with dry polished steel of 1 or less; and
  b) an endplate comprising a structural component able to engage a natural vertebral endplate or a bone or cartilage surface at or near a joint, a first low-friction surface that engages the elastomer layer, and a second low-friction surface that engages the curved surface of the hub, wherein the endplate, core or both are:
    i) circular, elliptical, or bean shaped and are inserted into the patient using an anterior approach of the spine;
    ii) crescent shaped and are inserted into the patient using a transforaminal approach of the spine;
    iii) elongated and are inserted into the patient using a direct lateral approach of the spine;
    iv) orbital shaped and are inserted into ball-and-socket joints such as the hip and shoulder; or
    v) radial or j-shaped and are inserted into hinge joints such as the knee and elbow.

12. The method of claim 11 wherein the prosthesis further comprises a torus collar on the surface of the hub and a corresponding negative space torus in the surface of the second low-friction surface, wherein said collar is able to be positioned into said negative space torus and reduce displacement of the core from the endplate and maintain and limit rotation of the components to approximately 90 degrees.

13. The method of claim 11 wherein the prosthesis further comprises a keystone component that is slidably engagable with the core and endplate, and wherein said keystone component locks the core and endplate together when engaged.

14. The method of claim 11 wherein the prosthesis further comprises one or more rails extending from the endplate and at least partially encasing the core, wherein said one or more rails are able to limit the amount of flexion and extension of the device to 60 degrees and lateral bending to 45 degrees.

15. The method of claim 11 wherein the structural component comprises a hollow and cylindrical mesh cage.

16. The method of claim 11 wherein said flange contains one or more negative spaces and said elastomer layer is molded around said flange and through said one or more negative spaces.

17. The method of claim 11 wherein the endplate further comprises a low-friction pad wherein the first low-friction surface which engages the elastomer layer is located on the surface of the low-friction pad.

18. The artificial joint of claim 17 wherein the low-friction pad has a coefficient of friction with dry polished steel of 0.3 or less.

19. The method of claim 11 wherein the curved surface of the hub has a coefficient of friction with dry polished steel of 1 or less.

* * * * *